(12) United States Patent
Kuo et al.

(10) Patent No.: US 8,502,967 B2
(45) Date of Patent: Aug. 6, 2013

(54) APPARATUS FOR OPTICAL INSPECTION

(75) Inventors: Cooper S. K. Kuo, Zhonghe District (TW); Ron Tsai, Zhonghe District (TW); Steven Lee, Zhonghe District (TW)

(73) Assignee: Cooper S. K. Kuo, New Taipai (TW)

( * ) Notice: Subject to any disclaimer, the term of this patent is extended or adjusted under 35 U.S.C. 154(b) by 0 days.

(21) Appl. No.: 13/051,874

(22) Filed: Mar. 18, 2011

(65) Prior Publication Data

US 2012/0194806 A1    Aug. 2, 2012

Related U.S. Application Data

(60) Provisional application No. 61/438,527, filed on Feb. 1, 2011.

(51) Int. Cl.
*G01N 21/00* (2006.01)

(52) U.S. Cl.
USPC .................................. 356/237.2; 356/237.1

(58) Field of Classification Search
USPC ............... 356/237.1–237.6, 51–68; 382/112, 382/100; 358/474, 400, 471
See application file for complete search history.

(56) References Cited

U.S. PATENT DOCUMENTS 7,852,982 B2 * 12/2010 Saito et al. .................. 378/58
2005/0040338 A1 * 2/2005 Weiss et al. ............... 250/358.1

OTHER PUBLICATIONS

U.S. Appl. No. 12/732,586, Mar. 26, 2010, Kuo et al.

* cited by examiner

*Primary Examiner* — Tri T Ton
(74) *Attorney, Agent, or Firm* — Abe Hershkovitz; Hershkovitz & Associates PLLC

(57) ABSTRACT

An apparatus for optical inspection comprises a platform extending in a first direction, a transmitting unit for transporting at least one carrier in the first direction from an input port to an output port thereof, each of the at least one carrier to support one of at least one object to be inspected, a first detector disposed above the platform and extending in a second direction orthogonal to the first direction for inspecting the at least one object on the at least one carrier, the first detector including a first scanner extending in the second direction between the input port and the output port, and a first roller set between the first scanner and the input port to apply force onto a surface of each of the at least one object.

10 Claims, 20 Drawing Sheets

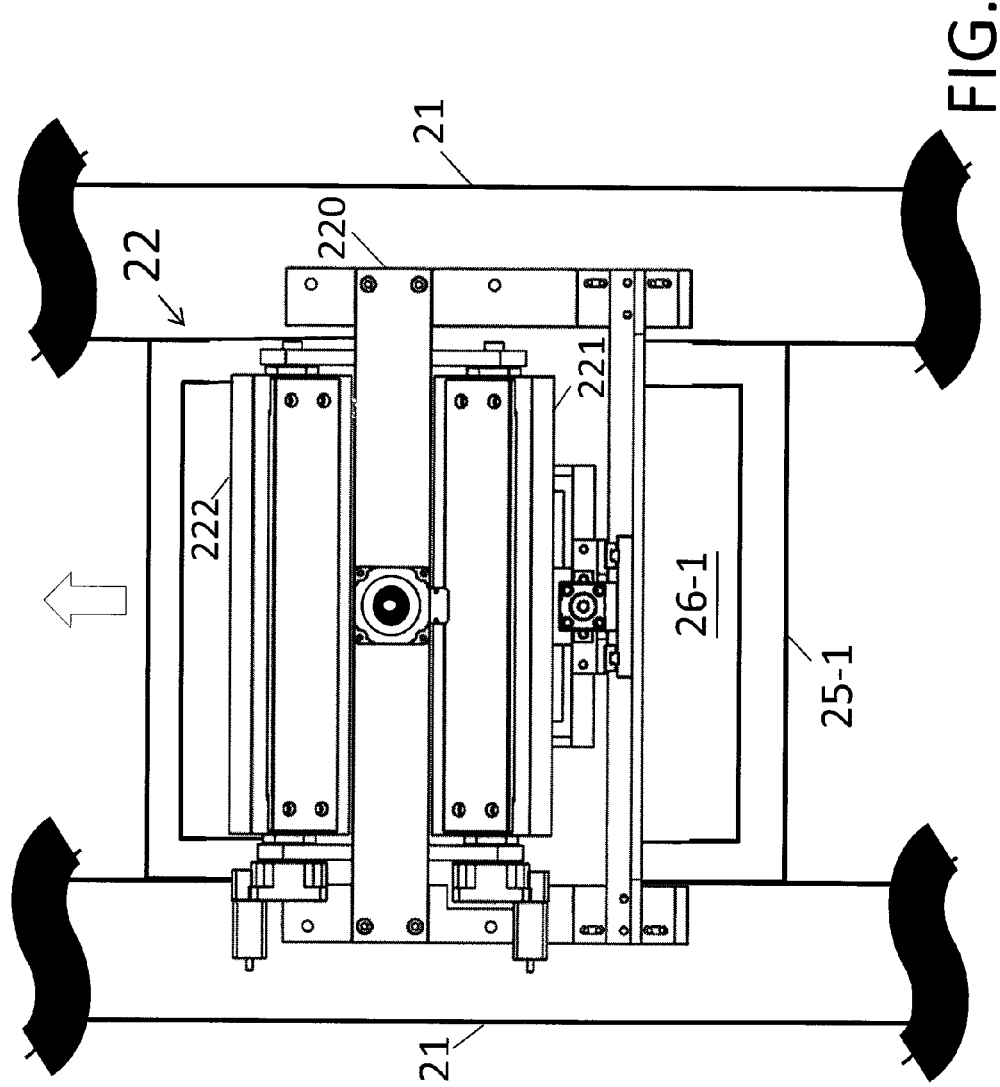

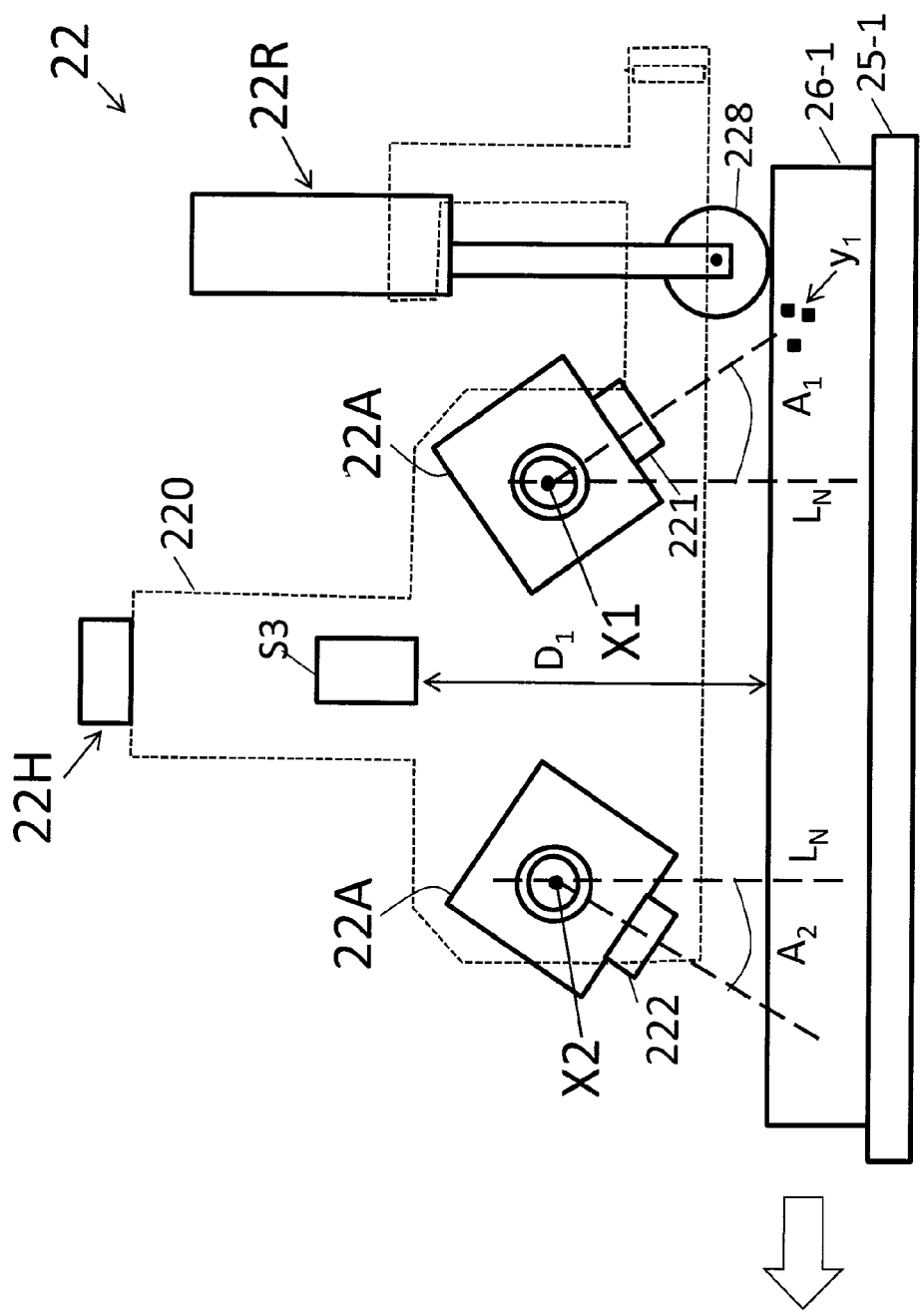

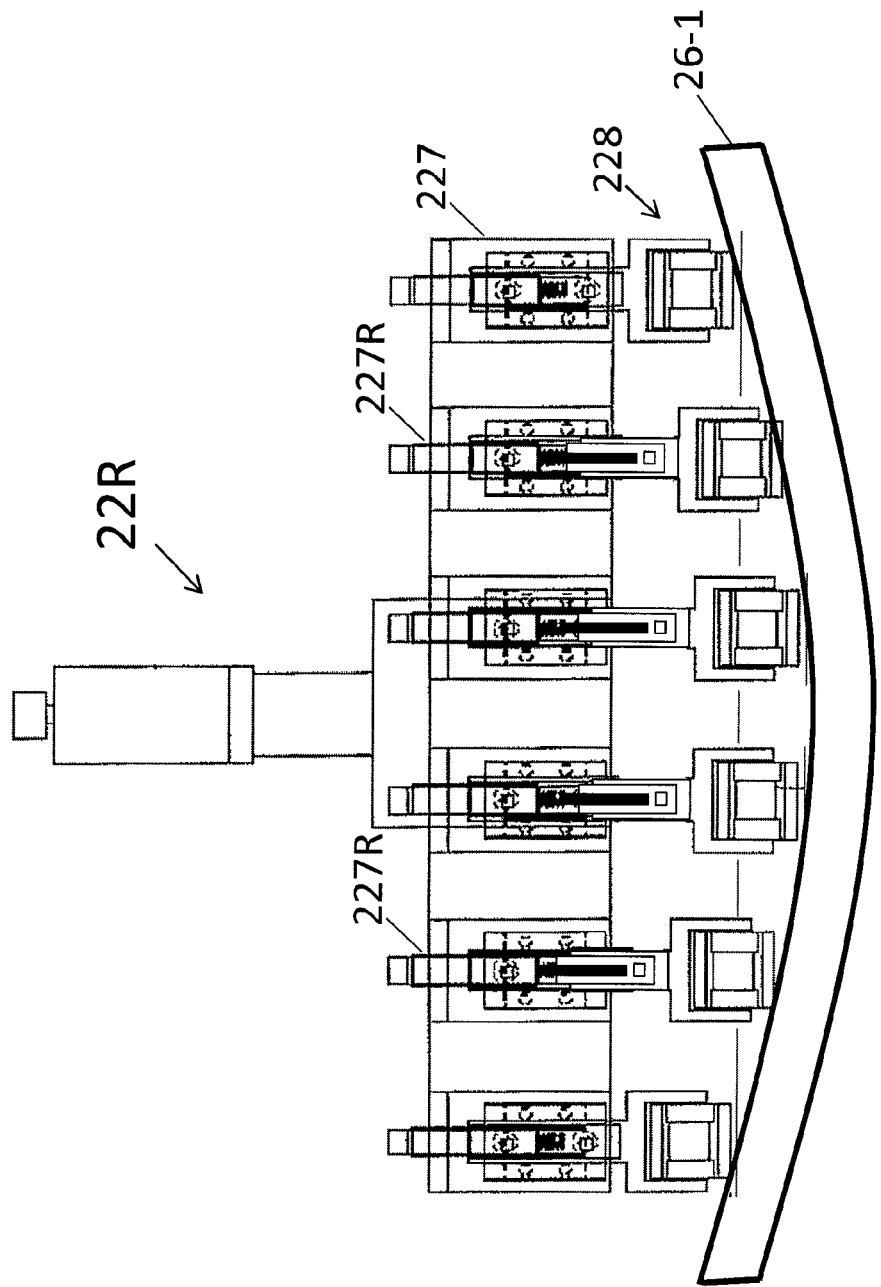

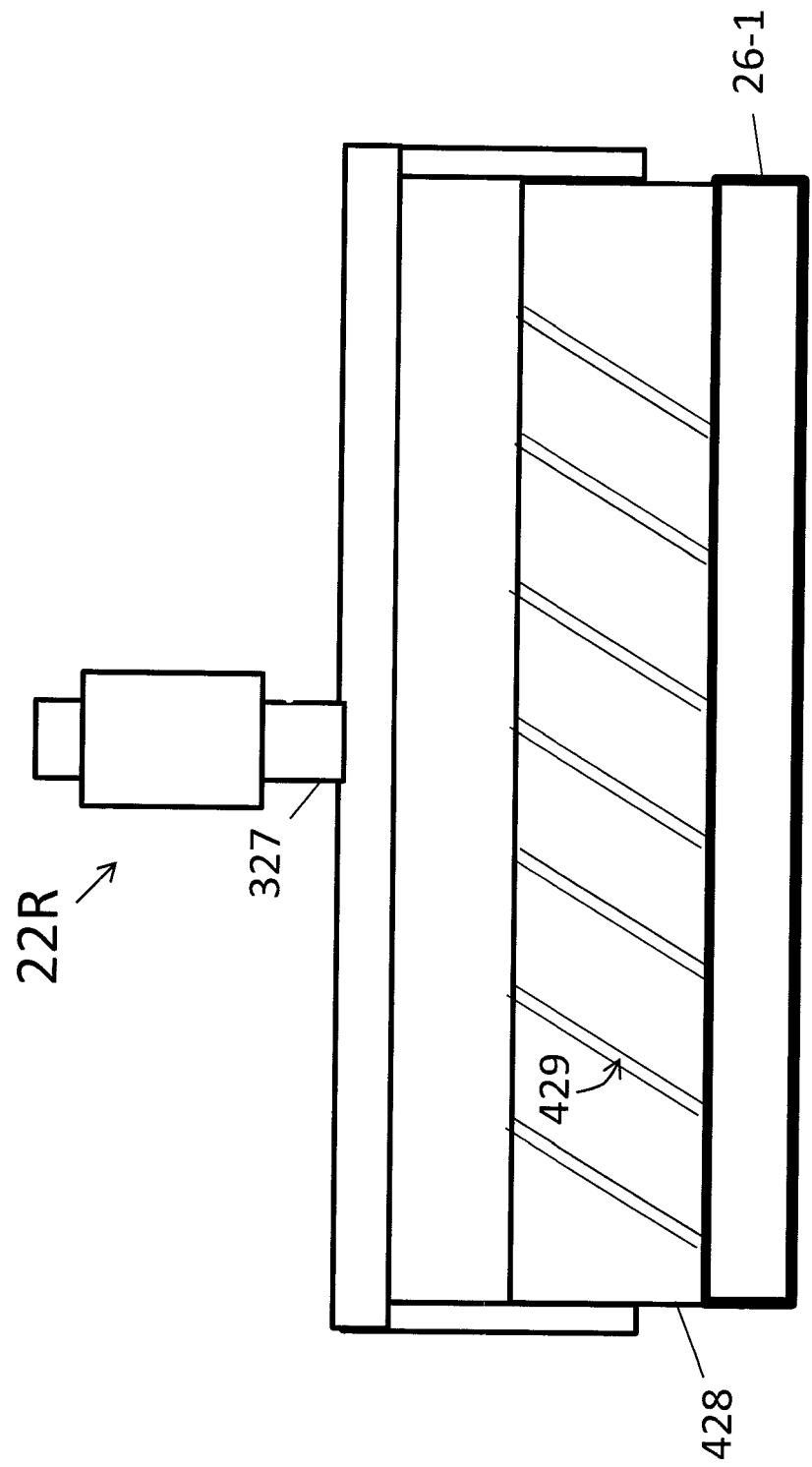

APPARATUS FOR OPTICAL INSPECTION

CROSS-REFERENCE TO RELATED APPLICATION

This application is a nonprovisional completion application of U.S. Provisional Application No. 61/438,527, filed Feb. 1, 2011, and the disclosure of which is incorporated herein by reference in its entirety.

BACKGROUND OF THE INVENTION

The invention generates relates to optical inspection and, more particularly, to an apparatus for inspecting defects or features of an object of interest.

Display devices such as liquid crystal display (LCD) devices are used for electronically displaying information including text, images and moving pictures. An LCD may include a number of layers such as polarized filter, glass substrate, color filter, liquid crystal and reflective surface, which may determine the quality of the LCD. To examine whether an LCD is a qualified one, that is, whether the LCD has defects less than a predetermined amount, human eye inspection may sometimes be employed. However, eye inspection may mean time-consuming, laborious and imprecise in the mass-production of LCDs. Moreover, with the advance in semiconductor manufacturing, it may become more difficult to examine LCD products with down-sized features by human eye inspection. Accordingly, inspection systems or apparatuses for automatic inspection of LCD panels have been developed. Nevertheless, some automatic scanning systems may not be able to identify defects of optical characteristics, which may not become visible or detectable unless viewed in a specific direction. Furthermore, during an inspection process, alien articles such as dirt or dust may be mistaken as defects. Moreover, it may be necessary to manually turn on a panel priot to inspection, which makes such scanning systems not so automatic.

It is therefore desirable to have an apparatus that is able to identify defects of optical characteristics and remove alien articles on a panel surface during inspection. Furthermore, it may also be desirable to have an apparatus that is able to supply power to a panel under inspection.

BRIEF SUMMARY OF THE INVENTION

Examples of the present invention may provide an apparatus for optical inspection. The apparatus comprises a platform extending in a first direction, a transmitting unit for transporting at least one carrier in the first direction from an input port to an output port thereof, each of the at least one carrier to support one of at least one object to be inspected, a first detector disposed above the platform and extending in a second direction orthogonal to the first direction for inspecting the at least one object on the at least one carrier, the first detector including a first scanner extending in the second direction between the input port and the output port, and a first roller set between the first scanner and the input port to apply force onto a surface of each of the at least one object.

Some examples of the present invention may also provide an apparatus for optical inspection. The apparatus includes a first apparatus unit comprising a first platform extending in a first direction, a first transmitting unit for transporting a carrier in the first direction from a first input port to a first output port thereof, and a first detector disposed above the first platform and extending in a second direction orthogonal to the first direction for inspecting an object on the carrier lengthwise, and a second apparatus unit comprising a second platform extending in the second direction, a second transmitting unit for transporting the carrier in the second direction from a second input port to a second output port thereof, and a second detector disposed above the second platform and extending in the first direction for inspecting the object on the carrier widthwise.

Examples of the present invention may still provide an apparatus for optical inspection. The apparatus includes a platform extending in a first direction, a first detector disposed above the platform and extending in a second direction orthogonal to the first direction for inspecting an object, and a transmitting unit for transporting a carrier in the first direction from an input port to an output port thereof, wherein the carrier has a first surface to support the object thereon and a second surface on which a power control unit to control supply of power to the object is provided, the carrier including a pair of conducting rails on the second surface to electrically couple the power control unit to a power source via the transmitting unit as the carrier is transported by the transmitting unit during inspection.

Additional features and advantages of the present invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The following detailed description of the invention will be better understood when read in conjunction with the appended drawings. For the purpose of illustrating the invention, examples are shown in the drawings. It should be understood, however, that the invention is not limited to the precise arrangements and instrumentalities shown in the examples.

In the drawings:

FIG. 3A is a top view of a detector of the apparatus illustrated in FIG. 1;

FIG. 3C is a left-side schematic view of the apparatus illustrated in FIG. 1;

FIG. 3E is a schematic view of a roller adjusting mechanism according to an example of the present invention;

FIG. 3G is a schematic view of a roller adjusting mechanism according to yet another example of the present invention;

FIGS. 7-1 to 7-6 are schematic diagrams of panels of different sizes to which a carrier according to the present invention may be applied;

DETAILED DESCRIPTION OF THE INVENTION

Reference will now be made in detail to the present examples of the invention, examples of which are illustrated in the accompanying drawings. Wherever possible, the same reference numbers will be used throughout the drawings to refer to the same or like parts.

Figure 1:
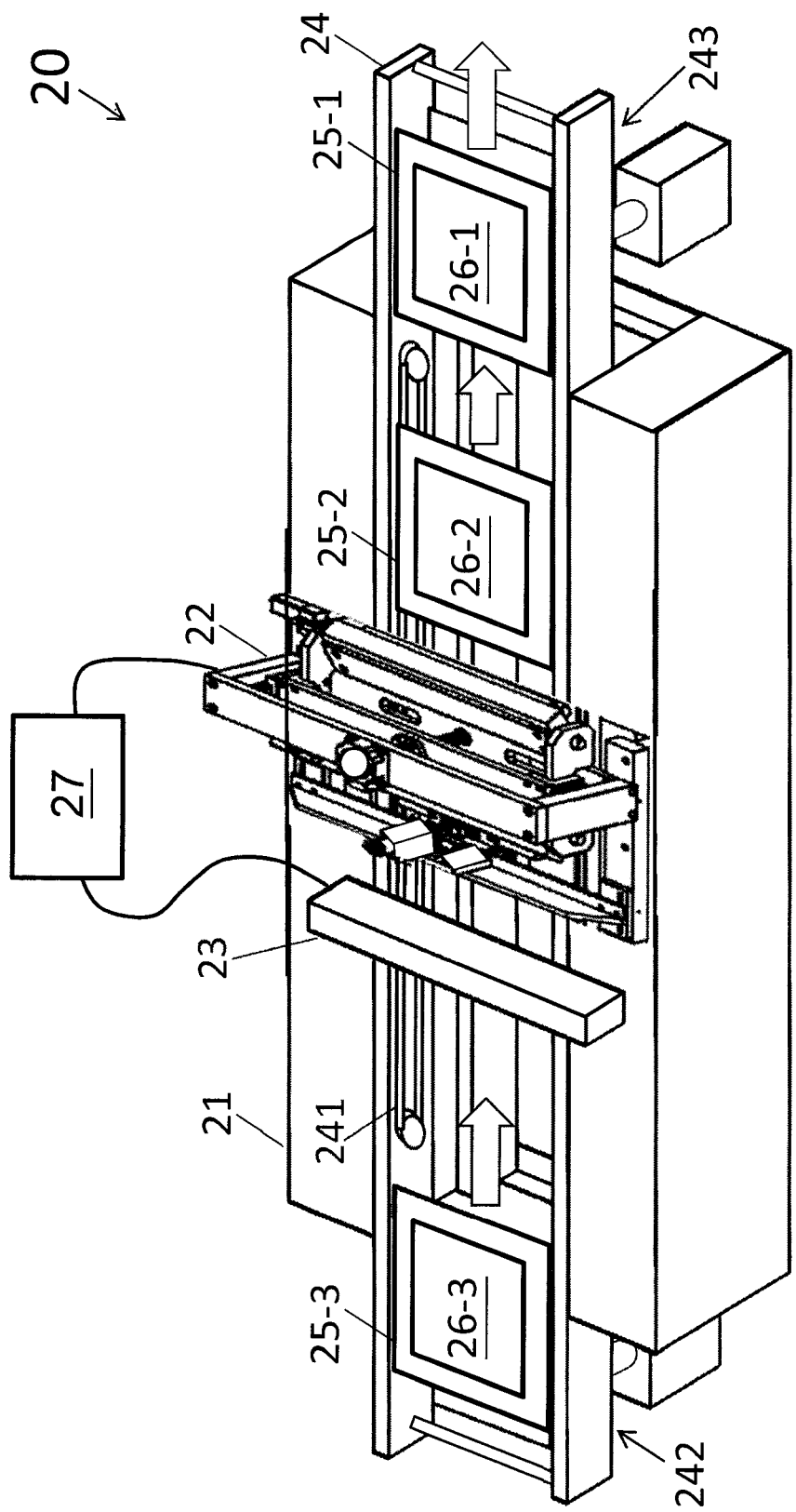
FIG. 1 is a schematic diagram of an apparatus for optical inspection in accordance with an example of the present invention.

FIG. 1 is a schematic diagram of an apparatus 20 for optical inspection in accordance with an example of the present invention. Referring to FIG. 1, the apparatus 20 may include a platform 21, a detector 22, a cleaner 23, a transmitting unit 24, a plurality of carriers 25-1, 25-2 and 25-3 to respectively carry objects 26-1, 26-2 and 26-3 under inspection, and a controller 27.

The platform 21 may serve as a working stage for optical inspection. In one example according to the present invention, the platform 21 may include a metal framework and extend in a first direction. Moreover, the platform 21 may be designed with a length to allow, for example, six objects in procession.

The transmitting unit 24 may include a set of conveyor belt 241 and guide rail (not shown) for the transportation of the objects 26-1 to 26-3 in the first direction from an input port 242 to an output port 243 thereof.

The detector 22 may include one or more scanner for inspecting the objects 26-1 to 26-3. The scanner may include one described and illustrated in U.S. patent application Ser. No. 12/732,586, entitled "Inspection System", filed Mar. 26, 2010 by Cooper S. K. Kuo and Ron Tsai, the same inventors of the subject application. The detector 22 may be disposed above the platform 21 and extend in a second direction substantially orthogonal to the first direction.

The cleaner 23 may be used to remove alien articles such as dust or dirt that may be caught on the surface of an object under inspection due to environmental factors. Such alien articles, if not properly removed, may be detected by the detector 22 and may be mistaken as defects of the object under inspection, which is not acceptable when a high defect identification rate is required. The cleaner 23 may be disposed between the input port 242 and the detector 22 and may extend in the second direction.

Figure 2:
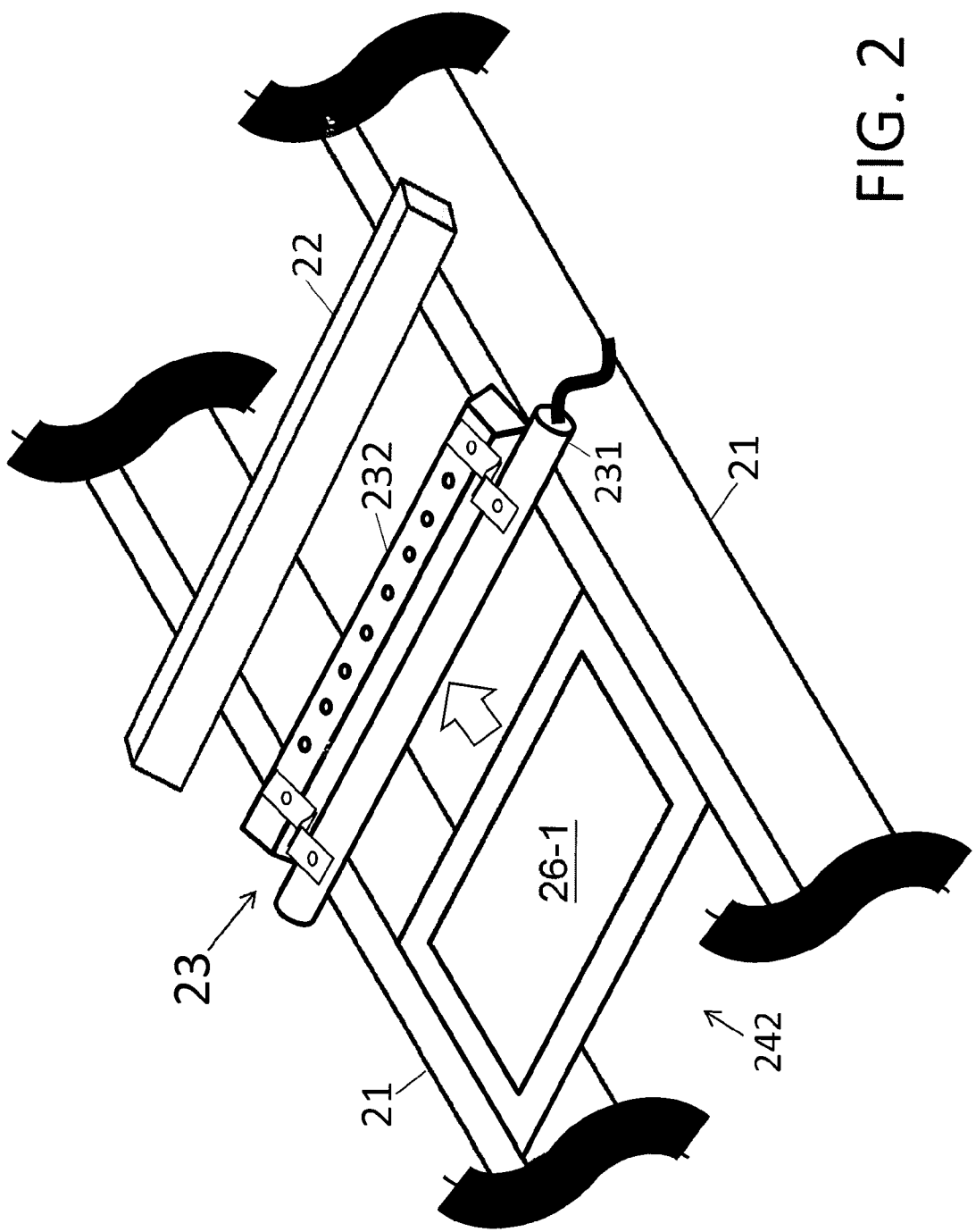
FIG. 2 is an enlarged view of a cleaner of the apparatus illustrated in FIG. 1.

FIG. 2 is an enlarged view of the cleaner 23 of the apparatus 20 illustrated in FIG. 1. Referring to FIG. 2, the cleaner 23 may include an ion remover 231 and an air knife 232. The ion remover 231, disposed between the input port 242 and the air knife 232, may de-ionize undesired or alien articles on an object under inspection, for example, the object 26-1, as the object 26-1 is transmitted in the first direction toward the detector 22. Then, the de-ionized articles may be easily removed by an air flow from the air knife 232. In one example according to the present invention, the ion remover 231 may include but is not limited to the ionizing bar "EI RN" manufactured by HAUG Ionization™, and the air knife 232 may include but is not limited to the "silent x-stream™ air blade™" air knife manufactured by NEX FLOW™.

Referring back to FIG. 1, the carriers 25-1 to 25-3 have a size suitable to support the objects 26-1 to 26-3 and fit within, for example, the guide rail of the transmitting unit 24. In one example according to the present invention, as will be further discussed, the objects 26-1 to 26-3 may include but are not limited to liquid crystal display (LCD) panels having a size of, for example, thirteen, fourteen and fifteen inches. The carriers 25-1 to 25-3 are sized to fit the LCD panels of different sizes. Moreover, as will be also discussed, the carriers 25-1 to 25-3 may be powered by an exterior power source through the transmitting unit 24 so as to turn on the LCD panels to facilitate inspection.

The controller 27 may be coupled with the cleaner 23, detector 22 and a set of sensors (not shown) in order to control the processing of inspection. The set of sensors may be disposed at desired locations in the platform 21 to facilitate the inspection. Furthermore, the controller 27 may be configured to collect scanned data associated with an object from the detector 22, analyze the scanned data and display the inspection result of a specific object on a monitor (not shown) in real time.

In operation, the first object 26-1 is positioned on the first carrier 25-1 before they are together placed at the input port 242. The first object 26-1 is then transmitted by the transmitting unit 24 in the first direction toward the output port 243. With the help of a first sensor (not shown), the first object 26-1 may be detected as it draws near the cleaner 23, and the controller 27 may then cause the cleaner 23 to function in response to the upcoming first object 26-1. Next, the first object 26-1 may be scanned by the detector 22. With the help of a second sensor (not shown), a first bar code (not shown) associated with the first object 26-1 that distinguishes the first object 26-1 from others may be identified. The scanned data and the identified bar code may be collected by the controller 27. In one example according to the present invention, when the first object 26-1 subsequently travels to the output port 243, the scanned data of the first object 26-1 may be simultaneously displayed. Furthermore, the controller 27 may cause an alarm device (not shown) to give off sound or light if the number of defects of an object exceeds a predetermined value.

The second object 26-2 together with the second carrier 25-2 may be placed at the input port 242 as the first object 26-1 travels down the first direction. For example, the second object 26-2 may be placed at the input port 242 when the first object 26-1 arrives at the cleaner 23 or the detector 22. Similarly, the third object 26-3 may be placed at the input port 242 when the second object 26-2 later arrives at the cleaner 23 or the detector 22. Furthermore, an object will be picked up when reaches the output port 243 to allow space for subsequent objects.

FIG. 3A is a top view of the detector 22 of the apparatus 20 illustrated in FIG. 1. Referring to FIG. 3A, the detector 22 may include a first scanner 221 and a second scanner 222, which are held by a support structure 220 at a desired elevation above the platform 21. The first and second scanners 221 and 222 may extend in the second direction and, as illustrated in the present example, scan the object 26-1 lengthwise as the object 26-1 travels in the first direction. Each of the first and second scanners 221 and 222 may include a number of scanning units arranged in the second direction that are sufficient to cover the width of the object 26-1.

Figure 3B:
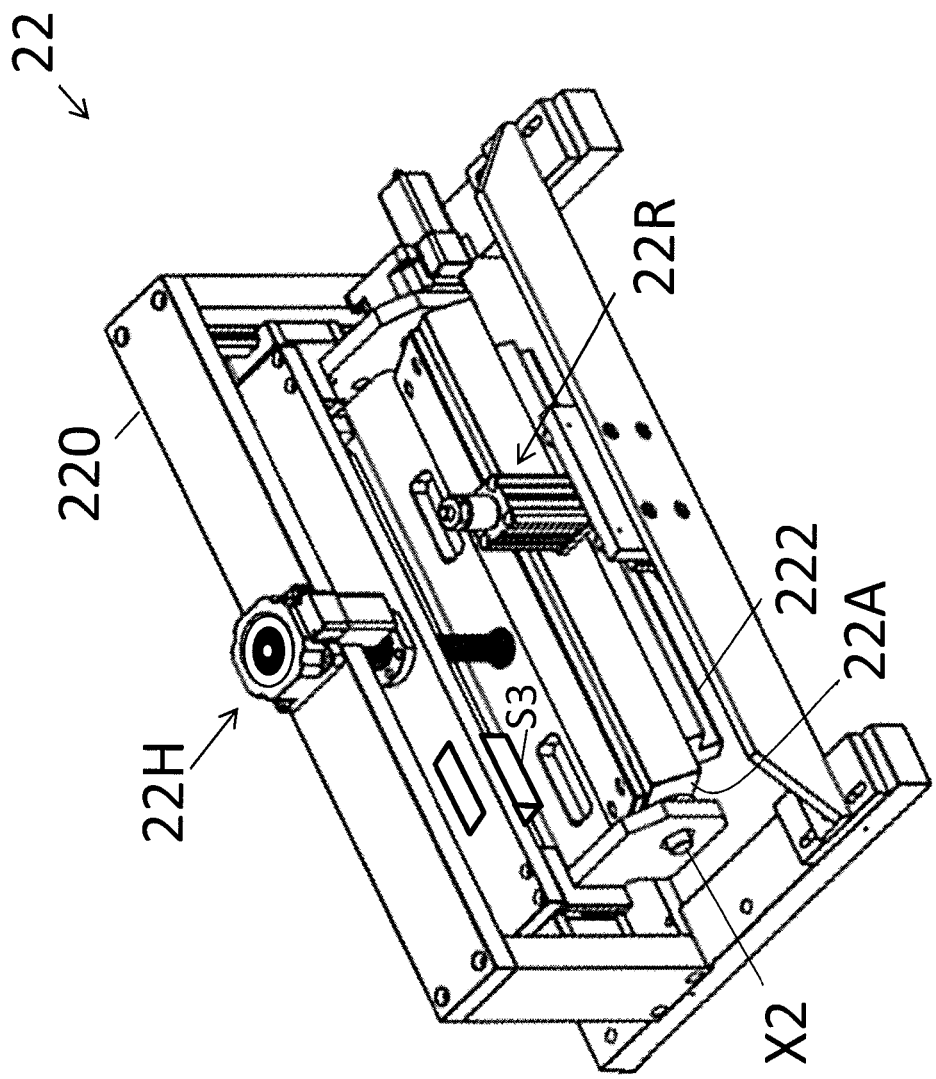
FIG. 3B is a rear elevation view of the detector of the apparatus illustrated in FIG. 3A.

FIG. 3B is a rear elevation view of the detector 22 of the apparatus 20 illustrated in FIG. 1. Referring to FIG. 3B, the apparatus 20 may further include a first adjusting means 22H to adjust the height or elevation of the detector 22 with respect to the platform 21 or an object. Specifically, the detector 22 may be adjusted to move upward or downward to a desired height in a third direction substantially orthogonal to the first direction and the second direction.

Moreover, the apparatus 20 may also include a second adjusting means 22R to adjust the force a set of rollers (not shown) may exert on the surface of an object under inspection, which will be further discussed below by reference to FIG. 3C. Furthermore, the apparatus 20 may still include one or more third adjusting means 22A to adjust an angle of the first and second scanners 221 and 222 with respect to the normal direction of the surface of an object under inspection.

FIG. 3C is a left-side schematic view of the apparatus 20 illustrated in FIG. 1. Referring to FIG. 3C, a third sensor S3 disposed at the support structure 220 (illustrated in dotted lines) may detect a distance $D_1$ from the surface of the object 26-1. The distance $D_1$ may be analyzed by the collector 27 to determine whether a desired height of the detector 22 is reached. If not, the detector 22 and thus the first and scanners 221 and 222 may be adjusted to a desired height through the first adjusting means 22H. In one example, the first adjusting means 22H may allow a manual adjustment. In another example, the first adjusting means 22H may allow an adjustment by the controller 27 by entering a command to the controller 27.

A first set of rollers 228 associated with the detector 22 may be arranged between the input port 242 and the first scanner 221 to press the surface of the object 26-1 so as to facilitate the subsequent scanning in the inspection process. Pressing an object before scanning may reduce the risk of mistaking a good pixel point as a defect and vice versa, in particular in the case of an object having a warp surface due to, for example, manufacturing factors. Furthermore, with the pressure from the first set of rollers 228, defects within an object may be more easily identified and distinguished from normal pixels in a region being pressed. In the present example, defects y1 in a region being pressed between the first set of rollers 228 and the first scanner 221 may become easily detectable. Moreover, to uniformly press the surface of an object, the first set of rollers 228 may be arranged to extend in the second direction and cover the width of the object that travels lengthwise in the first direction. The force or pressure the rollers 228 exert on the surface of the object 26-1 may be analyzed by the controller 27 and adjusted through the second adjusting means 22R, either manually or by way of the controller 27.

Figure 3D:
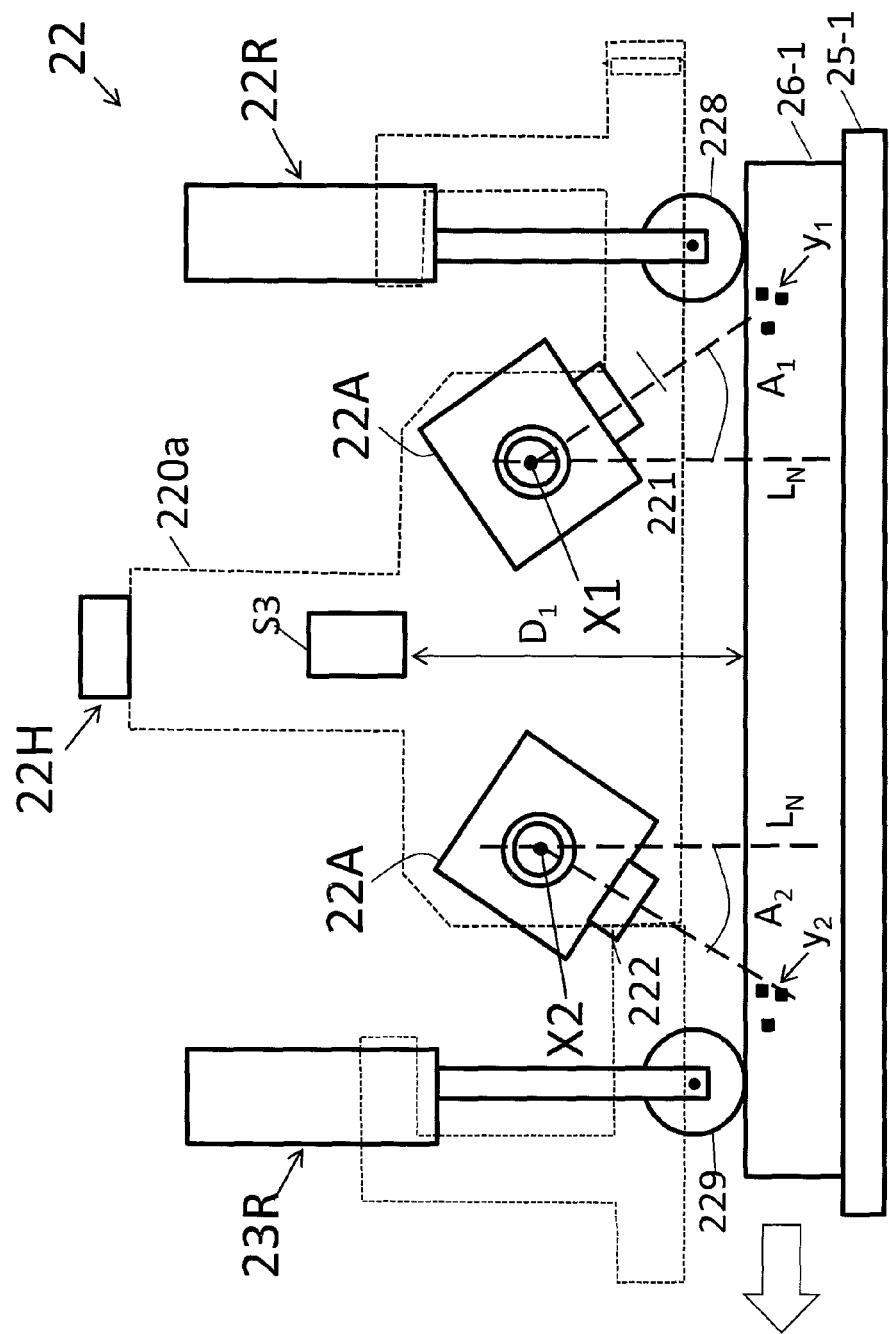
FIG. 3D is a left-side schematic view of the apparatus illustrated in FIG. 1 in accordance with another example of the present invention.

FIG. 3D is a left-side schematic view of the apparatus 20 illustrated in FIG. 1 in accordance with another example of the present invention. Referring to FIG. 3D, the detector 22 may further include a second set of rollers 229 disposed between the second scanner 222 and the output port 243 of the transmitting unit 24. In one example of the present invention, defects $y_2$ between the second set of rollers 229 and the second scanner 222 may become easily detectable. Furthermore, the second set of rollers 229 may be held and adjusted by a fourth adjusting means 23R, in a fashion similar to the first set of rollers 228.

FIG. 3E is a schematic view of a roller adjusting mechanism according to an example of the present invention. Referring to FIG. 3E, the roller adjusting mechanism may include the second adjusting means 22R and the first set of rollers 228. The second adjusting means 22R may include a roller support 227 to support the first set of rollers 228. In the present example, the roller support 227 includes a set of roller support units 227R each to support a corresponding one of the first set of rollers 228. Furthermore, each roller support unit 227R may be telescopic so that the elevation of a corresponding roller with respect to the object 26-1 and thus the force of the corresponding roller on the surface of the object 26-1 may be adjusted. In the case of a non-planar surface as illustrated in FIG. 3E, by adjusting each of the roller support units 227R, a uniform pressure across the non-planar surface may be achieved.

Figure 3F:
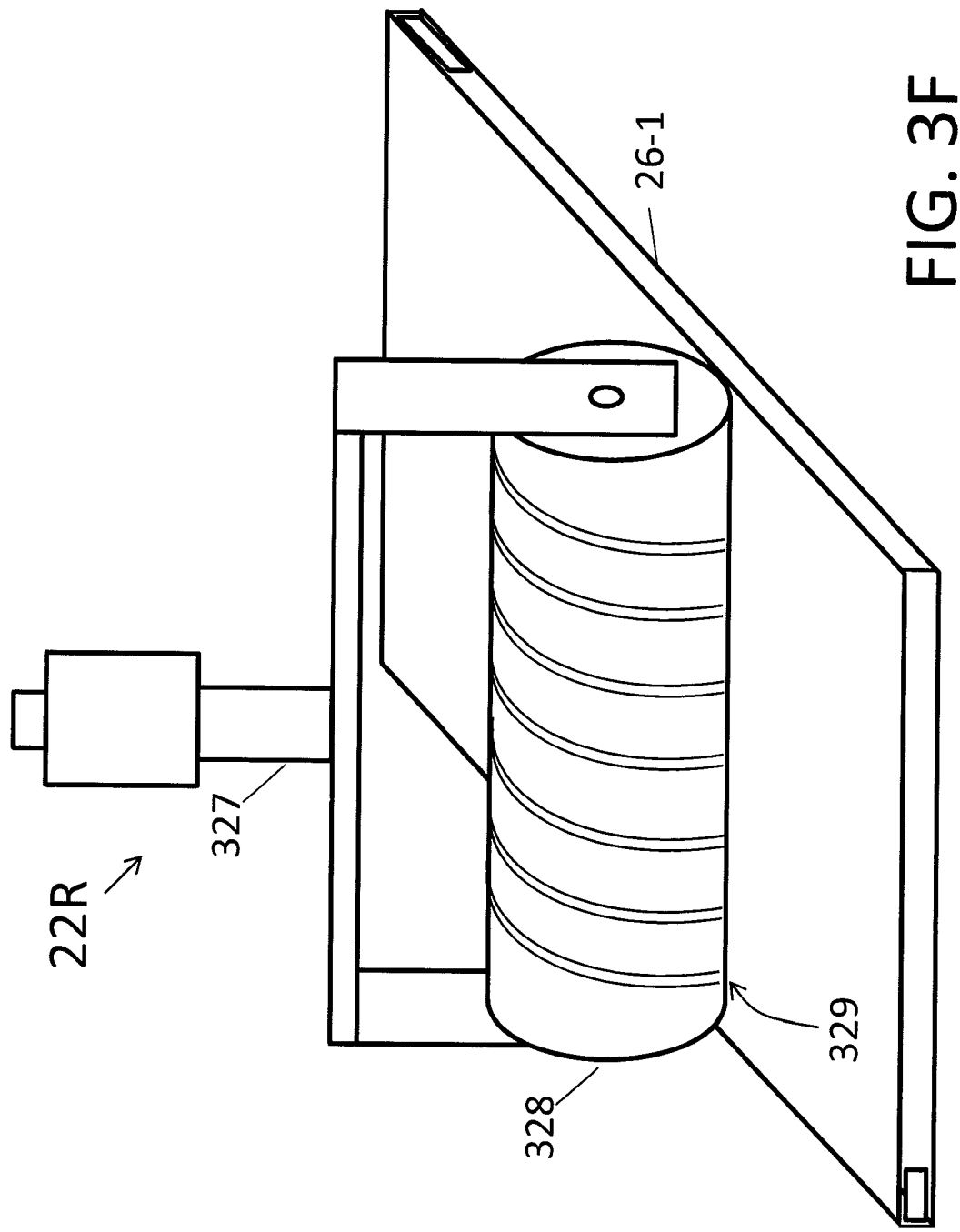
FIG. 3F is a schematic view of a roller adjusting mechanism according to another example of the present invention.

FIG. 3F is a schematic view of a roller adjusting mechanism according to another example of the present invention. Referring to FIG. 3F, the roller adjusting mechanism may include a roller support 327 and a single roller 328. The roller 328 may take the form of a cylinder with multiple straight grooves 329 on it. The force of the roller 327 on the object 26-1 may be controlled by a telescopic movement of the roller support 327 in the third direction.

FIG. 3G is a schematic view of a roller adjusting mechanism according to yet another example of the present invention. Referring to FIG. 3G, the roller adjusting mechanism may include a single roller 428 with diagonal grooves 429 on it.

Referring back to FIG. 3C, the first scanner 221 may be held in one of the third adjusting means 22A. An angle between the first scanner 221 and the normal direction (in the present example, the third direction) of the surface of the object 26-1 may be adjusted through the relevant third adjusting means 22A. Specifically, the first scanner 221 may be rotated about a first axis X1 to a first desired angle, either manually or by way of the controller 27.

Similarly, the second scanner 222 may be held in the other one of the third adjusting means 22A. An angle between the second scanner 222 and the normal direction of the surface of the object 26-1 may be adjusted through the relevant third adjusting means 22A. Specifically, the second scanner 222 may be rotated about a second axis X2 to a second desired angle, either manually or by way of the controller 27. In one example according to the present invention, the angle each of the scanners 221 and 222 may rotate may range from approximately minus thirty degrees to plus thirty degrees (±30°). For example, the first scanner 221 may be rotated at a first angle $A_1$ ranging between 0 to 30 degrees with respect to a normal line $L_N$, while the second scanner 222 may be rotated at a second angle $A_2$ ranging between 0 and −30 degrees with respect to the normal line $L_N$. The view angle adjustment may facilitate an omni-directional detection so that defects such as dust or scratches with an optical orientation may be detectable at a specific angle.

Figure 4:
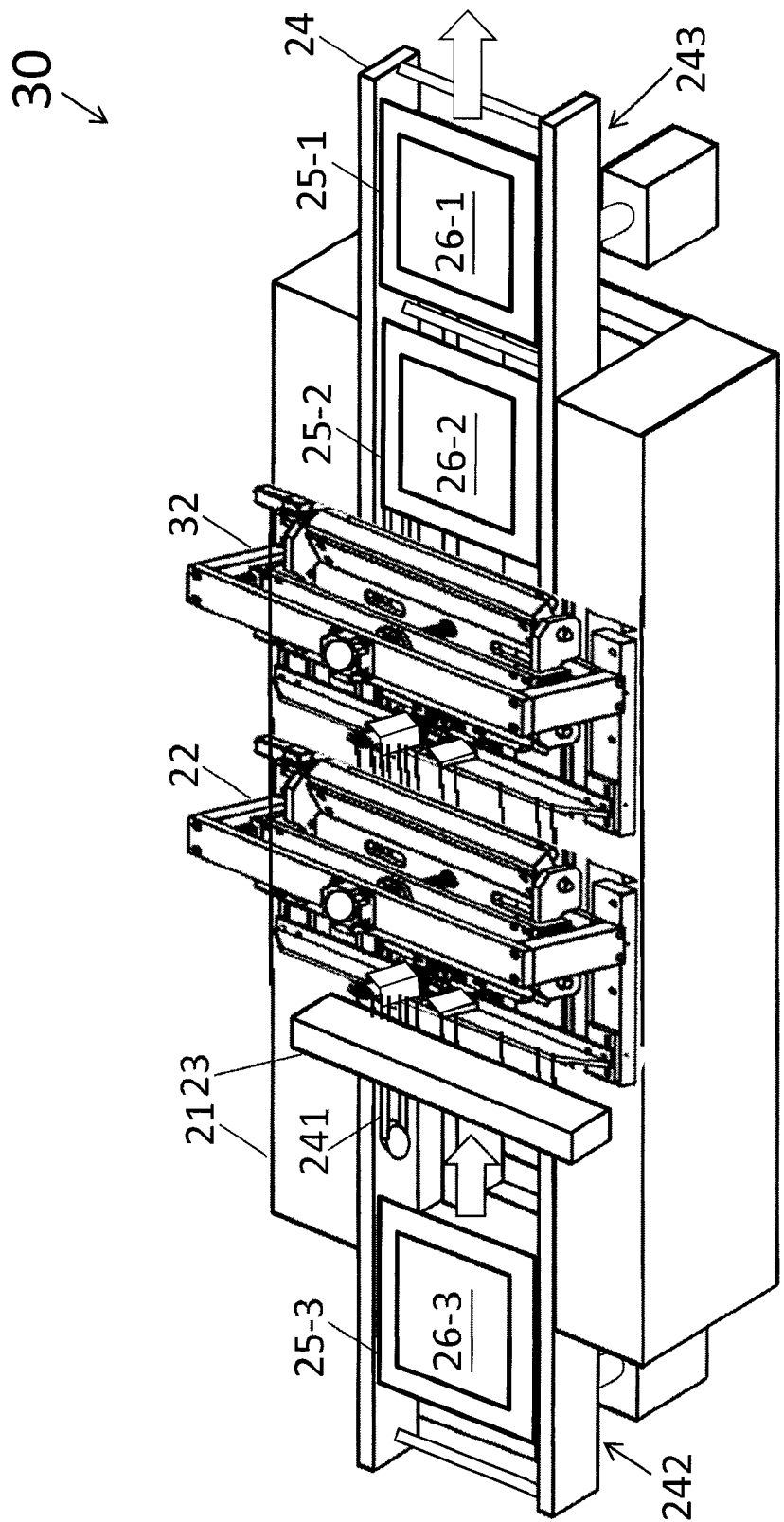
FIG. 4 is a schematic view of an apparatus for optical inspection in accordance with another example of the present invention.

FIG. 4 is a schematic view of an apparatus 30 for optical inspection in accordance with another example of the present invention. Referring to FIG. 4, the apparatus 30 may be similar to the apparatus 20 described and illustrated with reference to FIG. 1 except that, for example, another detector 32 is added. Specifically, the apparatus 30 includes a first scanner 22 between the input port 242 and the output port 243 and a second detector 32 between the first detector 22 and the output port 242. Furthermore, the second detector 32 in structure and function may be similar to or same as the first detector 22 and therefore is not further discussed. The apparatus 30 may be applied to scenarios where an object under inspection has multiple layers of interest, where a redundant scanning of an object is necessary or where a speedy scanning is required. In the scenario of speedy scanning, the first and second detectors 22 and 32 may scan two objects at one time. For example, in the order of transportation illustrated in FIG. 4, the second detector 32 may be assigned to scan the first object 26-1 while the first detector 22 to scan the second object 26-2 so as to double the scanning speed. Skilled persons in the art will realize that an apparatus according to the present invention may be provided with three or more detectors if the inspection process permits.

Figure 5A:
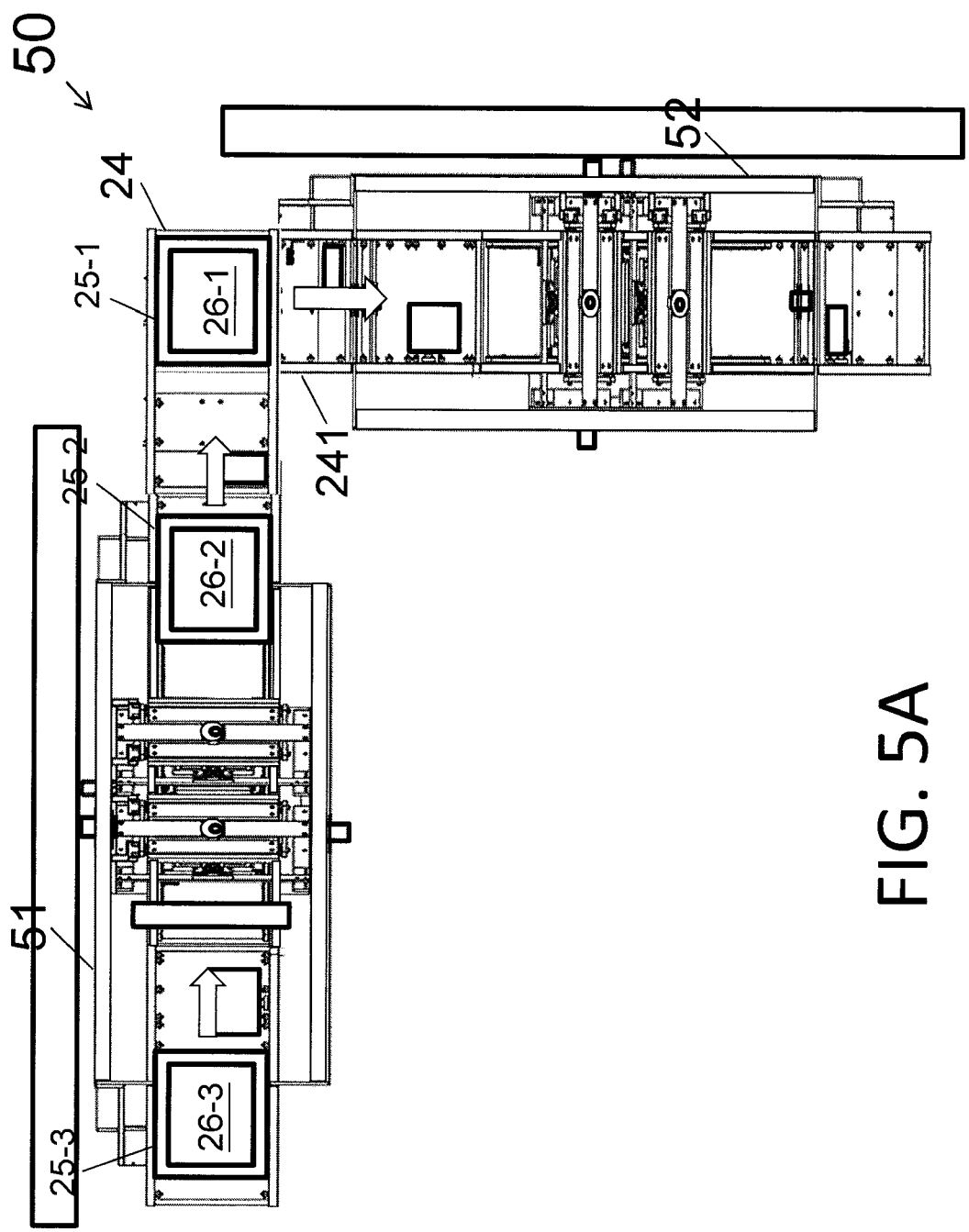
FIGS. 5A and 5B are schematic top views of an apparatus for optical inspection in accordance with still another example of the present invention.
Figure 5B:
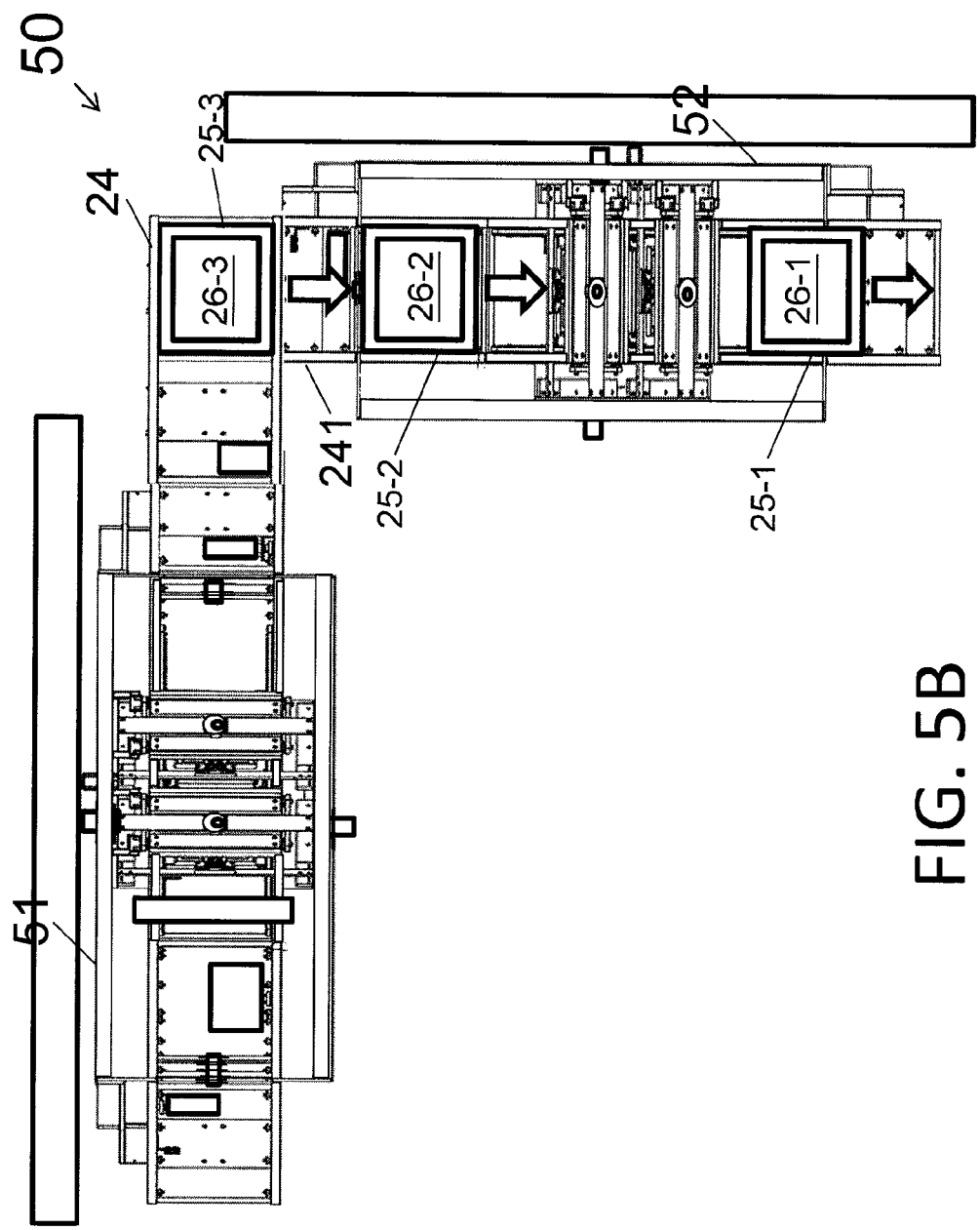

FIGS. 5A and 5B are schematic top views of an apparatus 50 for optical inspection in accordance with still another example of the present invention. Referring to FIG. 5A, the apparatus 50 may include a first apparatus unit 51 and a second apparatus unit 52. In the present example, the first apparatus unit 51 may include a cleaner and a pair of detectors, and may be similar to or same as the apparatus 30 illustrated in FIG. 4 in structure and function. Furthermore, the second apparatus unit 52 may include a pair of detectors and may be similar to the apparatus 30 illustrated in FIG. 4 in structure and function except that the second apparatus unit 52 may not include a cleaner as the first apparatus unit 51 since alien articles that may be caught on the surface of an object under inspection may have been removed by the cleaner of the first apparatus unit 51. In another example, the first and second apparatus units 51 and 52 each includes a single detector, and may be similar to or same as the apparatus 20 illustrated in FIG. 1 except that the second apparatus units 52 may not include a cleaner as the first apparatus units 51.

The first apparatus unit 51 may be arranged to transmit the objects 26-1 to 26-3 in the first direction and scan them lengthwise. Accordingly, defects due to narrow-beam illumination or only visible and detectable along the first direction may be detected by the scanners of the pair of detectors or the single detector of the first apparatus unit 51. On the other hand, the second apparatus unit 52 may be arranged to transmit the objects 26-1 to 26-3 in the second direction orthogonal to the first direction and scan them widthwise. Accordingly, defects only visible and detectable along the second direction may be detected by the scanners of the pair of detectors or the single detector of the second apparatus unit 52. To facilitate such scanning, the first apparatus unit 51 and the second apparatus unit 52 may be arranged to extend in directions orthogonal to each other, with the output port 243 of the first apparatus unit 51 being coupled to or serving as the input port 242 of the second apparatus unit 52.

In operation, the objects 26-1 to 26-3 may be placed at the input port 242 of the first apparatus unit 51, with a width side of each facing toward the output port 243 of the first apparatus unit 51 such that the objects 26-1 to 26-3 are scanned lengthwise as they travel down in the first direction in the first apparatus unit 51. Referring now to FIG. 5B, when the first object 26-1 reaches the output port 243 of the first apparatus unit 51, with its length side facing toward the input port 242 of the second apparatus unit 52, the object 26-1, so do the subsequent objects 26-2 and 26-3, is then scanned widthwise as it travels down in the second direction in the second apparatus unit 52.

Figure 6A:
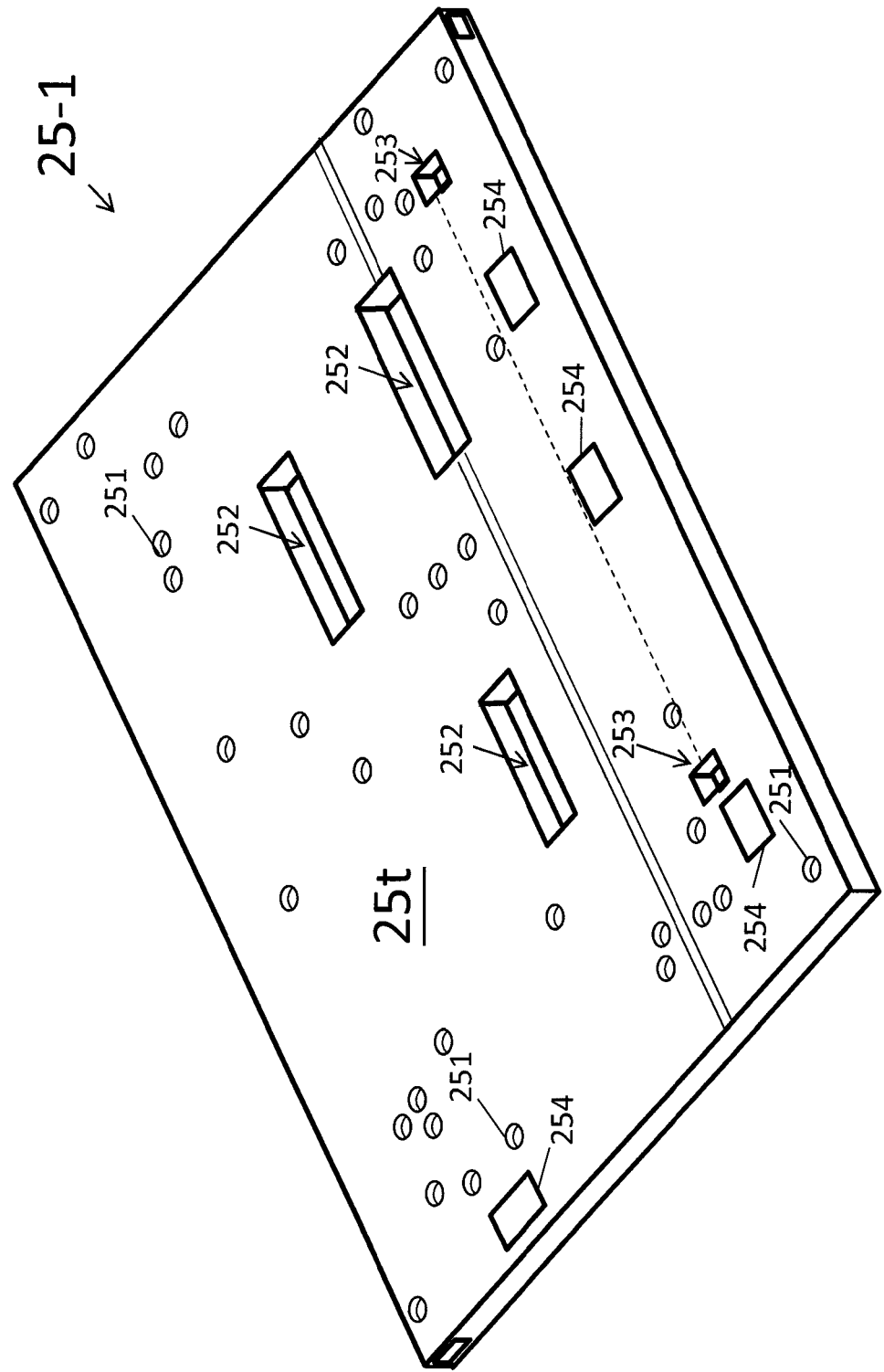
FIG. 6A is a top elevation view of a carrier in the apparatus for optical inspection illustrated in FIG. 1.
Figures 1, 7:
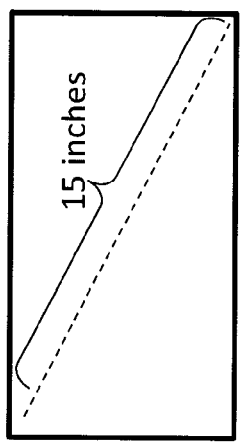
Figures 2, 7:
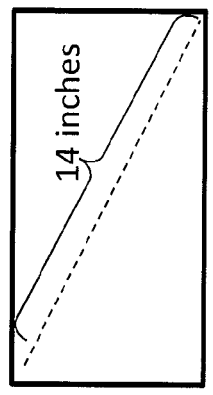
Figures 3, 7:
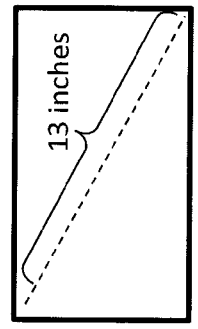
Figures 4, 7:
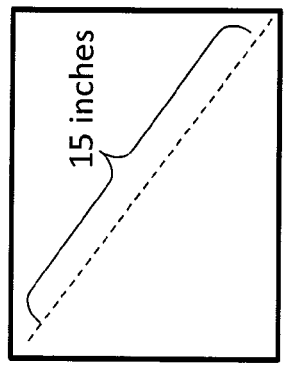
Figures 5, 7:
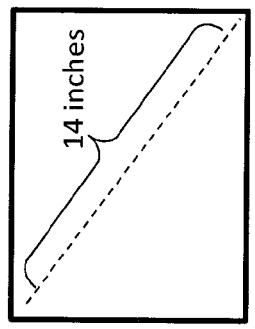
Figures 6, 7:
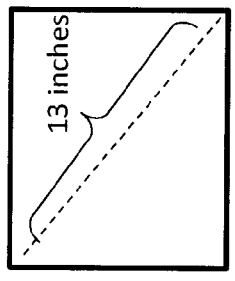

FIG. 6A is a top elevation view of the carrier 25-1 in the apparatus 20 for optical inspection illustrated in FIG. 1. Referring to FIG. 6A, the carrier 25-1 has a plurality of first openings 251, a plurality of second openings 252, a plurality of third openings 253 and a plurality of connectors 254. The first openings 251 may be arranged in a pattern so that the carrier 25-1, with the help of plugs, may be applicable to panels of different sizes. FIGS. 7-1 to 7-6 are schematic diagrams of panels of different sizes to which the carrier 25-1 according to the present invention may be applied. The panels may include but are not limited to thirteen-inch, fourteen-inch and fifteen-inch panels. Specifically, the panels illustrated in FIGS. 7-1 to 7-3 have an aspect ratio of 16 times 9, and the panels illustrated in FIGS. 7-4 to 7-6 have an aspect ratio of 4 times 3.

Referring back to FIG. 6A, the second openings 252, in the form of rectangular through holes extending in the first direction, may be arranged in a pattern in connection with a location of product information such as a panel bar code printed on a bottom surface of a panel. The bar code location may be different as the panel size is different. Accordingly, depending on the panel size, one of the second openings 252 may expose the bar code of a panel of a specific size.

The third openings 253 may be used to secure a panel onto the carrier 25-1. Like the first openings 251, the third openings 253 can keep a panel in place so that the panel is immobile with respect to the carrier 25-1 during inspection. Displacement of a panel on the carrier 25-1 may result in an inspection error such as a mismatch between a defect detected and its coordinates.

The connectors 254 may include conductive pads arranged on a top or first surface 25*t* of the carrier 25-1 to maintain an electrical connection with an exterior power source through the transmitting unit 24 during inspection.

Figure 6B:
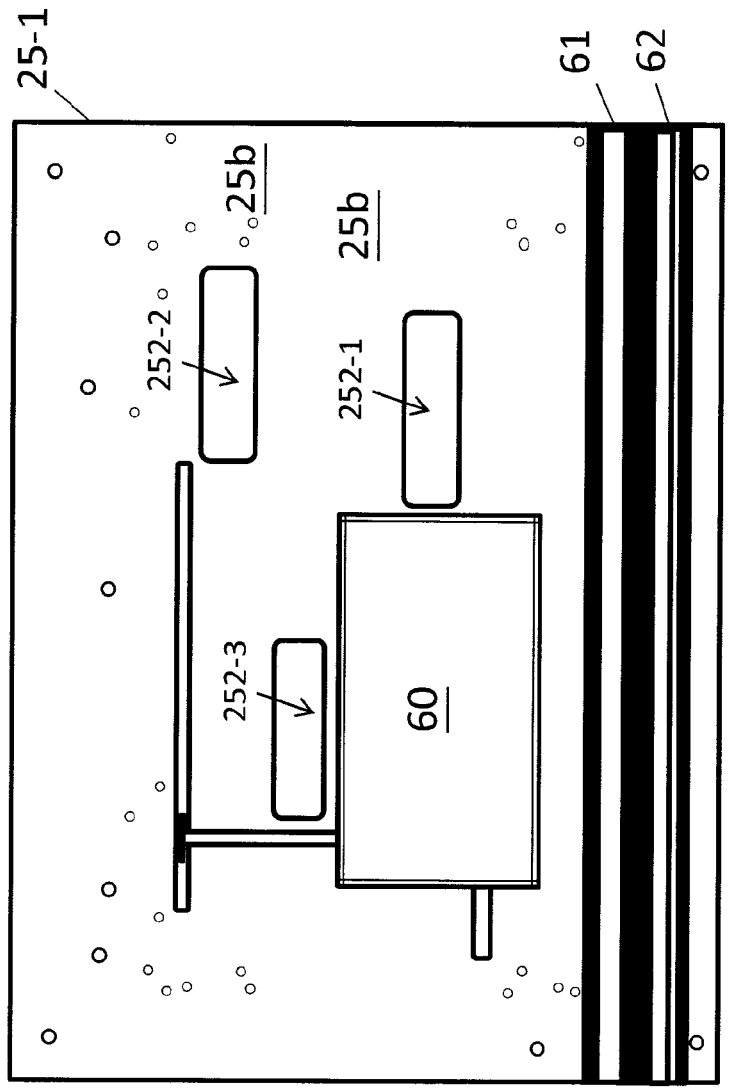
FIG. 6B is a bottom view of the carrier illustrated in FIG. 6A.

FIG. 6B is a bottom view of the carrier 25-1 illustrated in FIG. 6A. Referring to FIG. 6B, the carrier 25-1 may further include a power control unit 60 and a pair of conducting rails 61 and 62 on a bottom or second surface 25*b* of the carrier 25-1. The power control unit 60 may control supply of power to a panel, for example, a light source such as a backlight source of the panel. At least during an inspection period, the power control unit 60 is required to turn on the backlight source to facilitate the scanning of the panel and render defects such as bright dots or dark dots visible and detectable. Moreover, the conducting rails 61 and 62, extending in the first direction, may contact the transmitting unit 24 so as to electrically couple the power control unit 60 to the exterior power source through the connectors 254 and the transmitting unit 24.

Figure 8A:
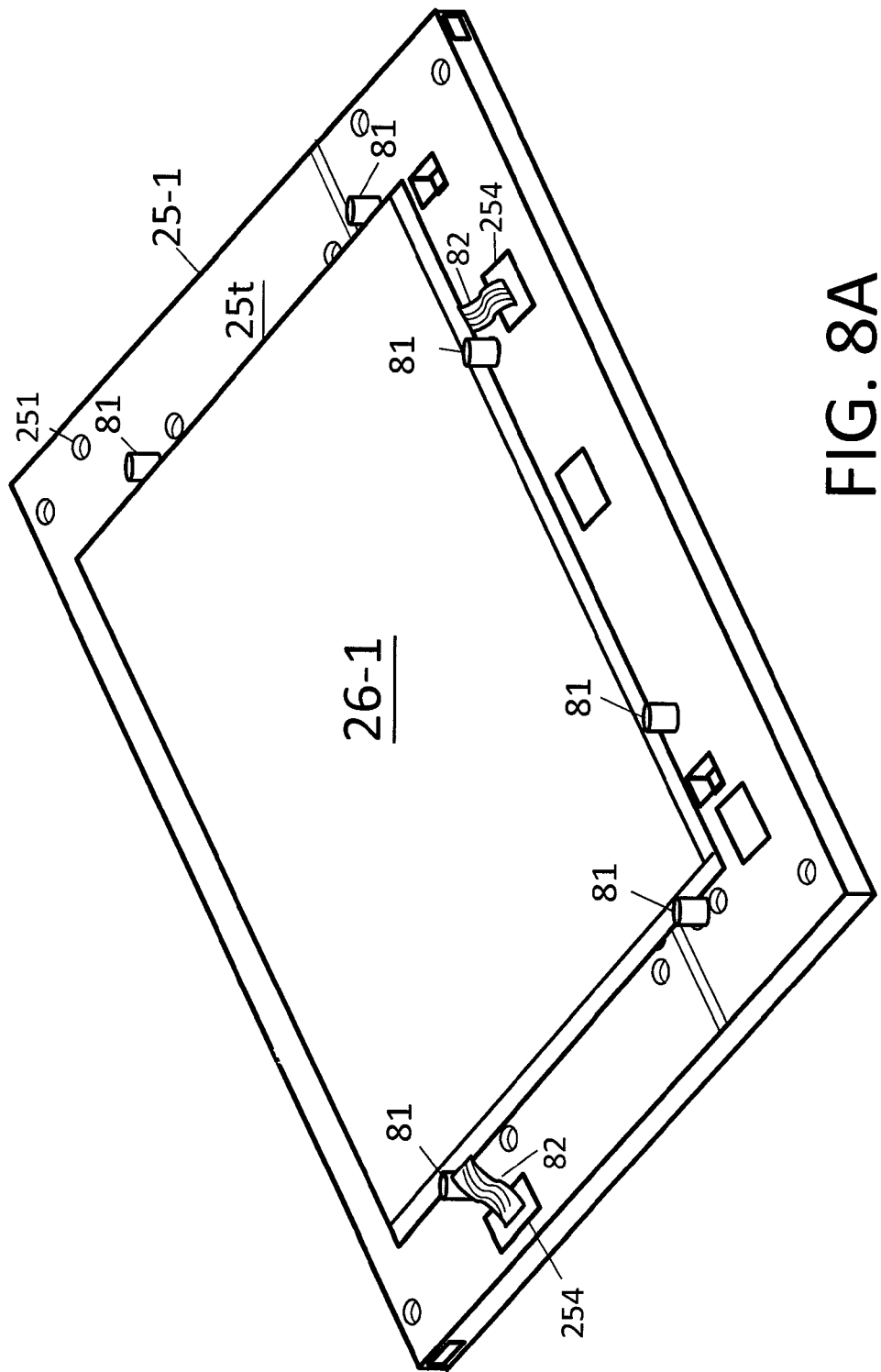
FIG. 8A is a top elevation view showing a carrier when a first object is secured thereto in accordance with an example of the present invention.

FIG. 8A is a top elevation view showing the carrier 25-1 when the first object 26-1 is secured thereto in accordance with an example of the present invention. Referring to FIG. 8A, a number of plugs 81, each being sized to be able to snugly fit within the first openings 251, may be inserted to a first selected group of the first openings 251 to secure the first object 26-1 of a first size on the first surface 25*t* of the carrier 25-1. Furthermore, flexible circuit boards (FCBs) 82 in electrical connection with light sources of the first object 26-1 may be coupled to a selected set of the connectors 254 so as to turn on the light sources to facilitate optical inspection. Moreover, the light sources may each include a cold cathode fluorescence lamp (CCFL) contained in a magnetic metal housing. In that case, the plugs 81 may be made of a magnetic material so as to further secure the first object 26-1.

Figure 8B:
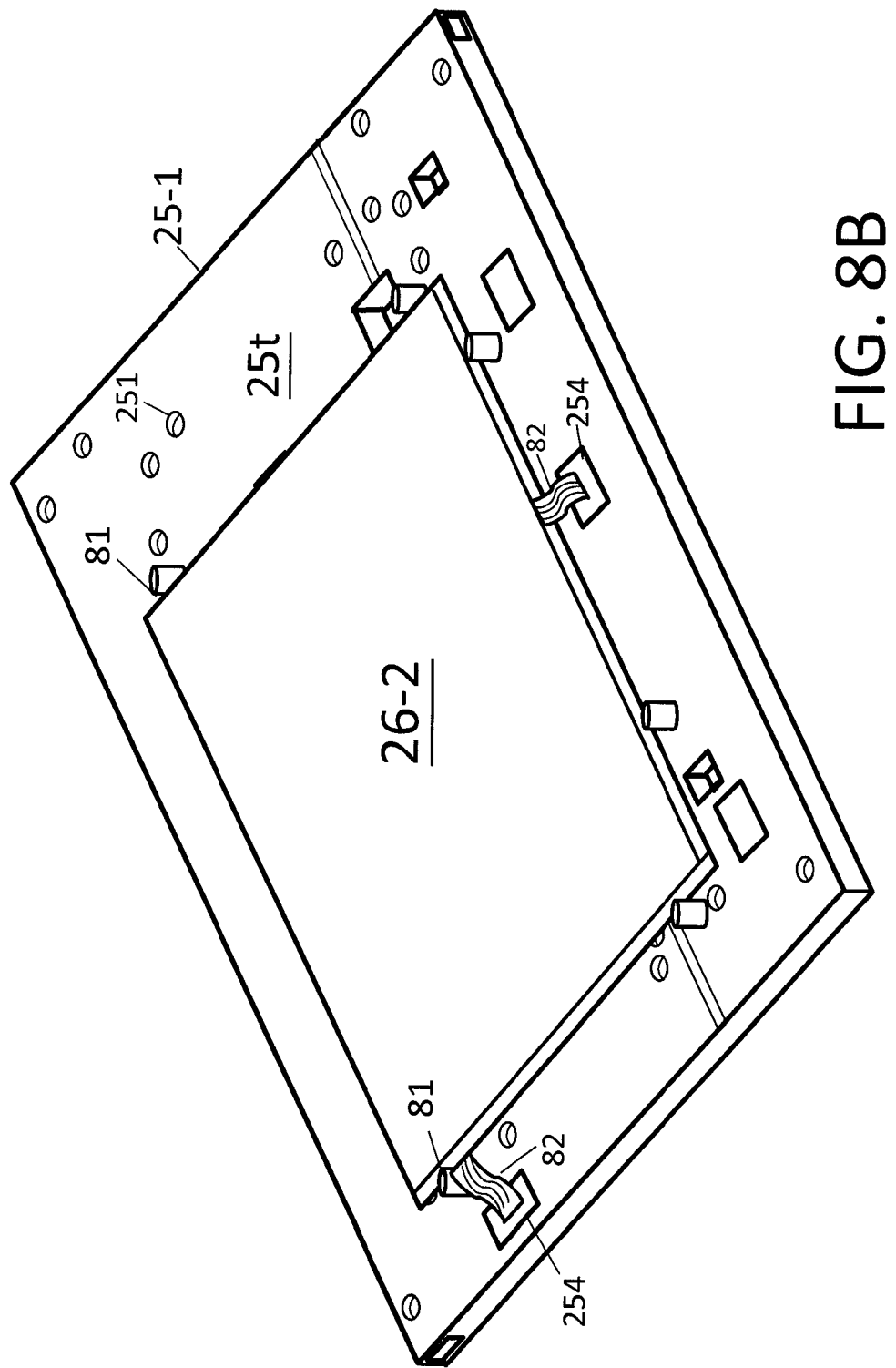
FIG. 8B is a top elevation view showing the carrier when a second object is secured thereto in accordance with an example of the present invention.

FIG. 8B is a top elevation view showing the carrier 25-1 when the second object 26-2 is secured thereto in accordance with an example of the present invention. Referring to FIG. 8B, a number of plugs 81 may be inserted to a second selected group of the first openings 251 to secure the second object 26-2 of a second size on the first surface 25*t* of the carrier 25-1. As compared to the first object 26-1 illustrated in FIG. 8A, the second size is smaller than the first size. Accordingly, with the help of the plugs 81 and by selecting a suitable set of the first openings 251 of a predetermined pattern, the carrier 25-1 is suitable for supporting panels of different sizes.

Figure 8C:
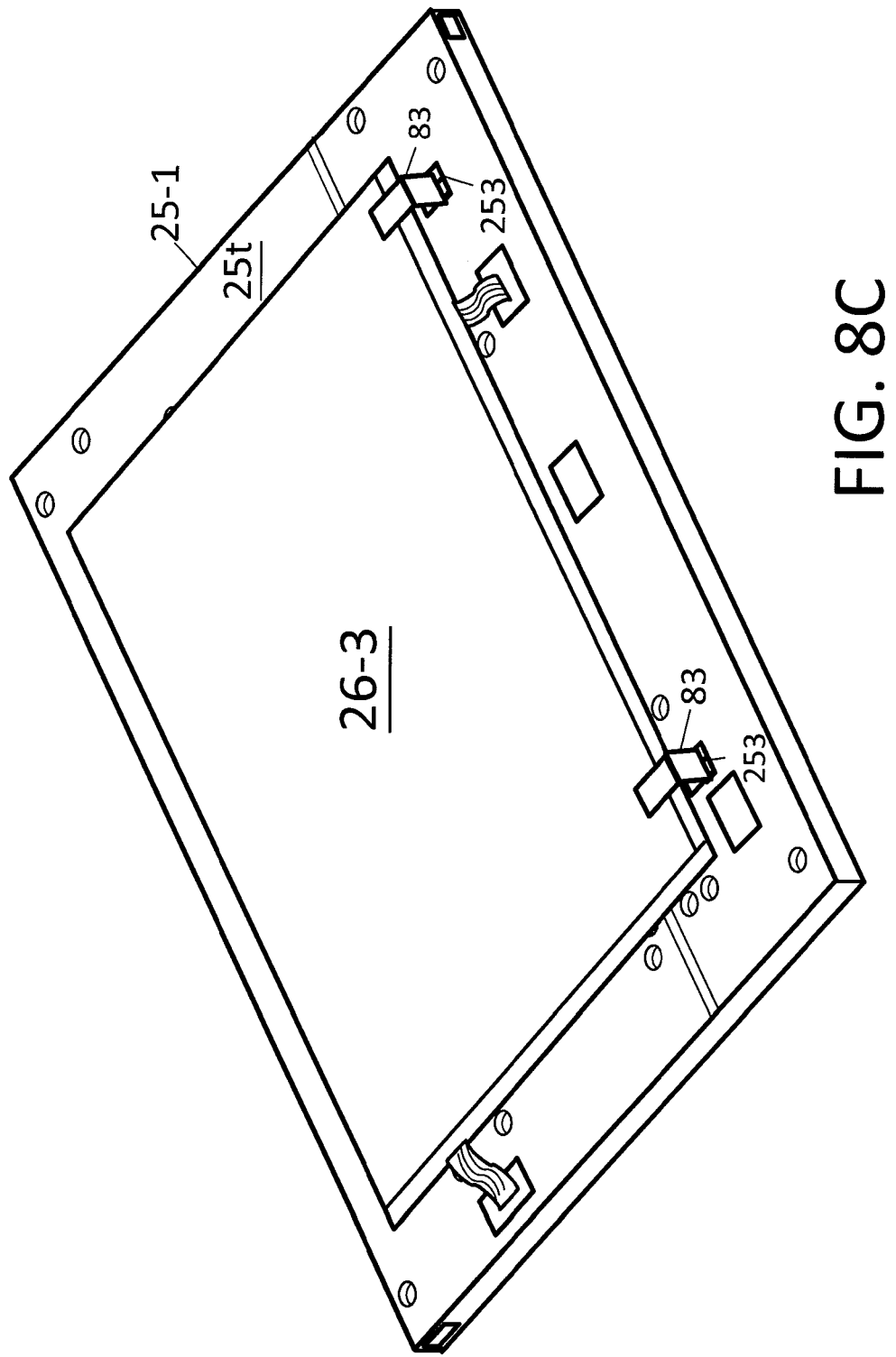
FIG. 8C is a top elevation view showing the carrier when a third object is secured thereto in accordance with an example of the present invention.

FIG. 8C is a top elevation view showing the carrier 25-1 when the third object 26-3 is secured thereto in accordance with an example of the present invention. Referring to FIG. 8C, a number of plugs 81 may be inserted to a third selected group of the first openings 251 to secure the third object 26-2 of a third size on the first surface 25t of the carrier 25-1. Moreover, the light sources of the third object 26-3 may each include light emitting diode (LED) strings that may be covered by a plastic shroud. In that case, clips 83 with one end in the third openings 253 may secure the third object 26-3 on the first surface 25t of the carrier 25-1 with the other end.

Figure 9A:
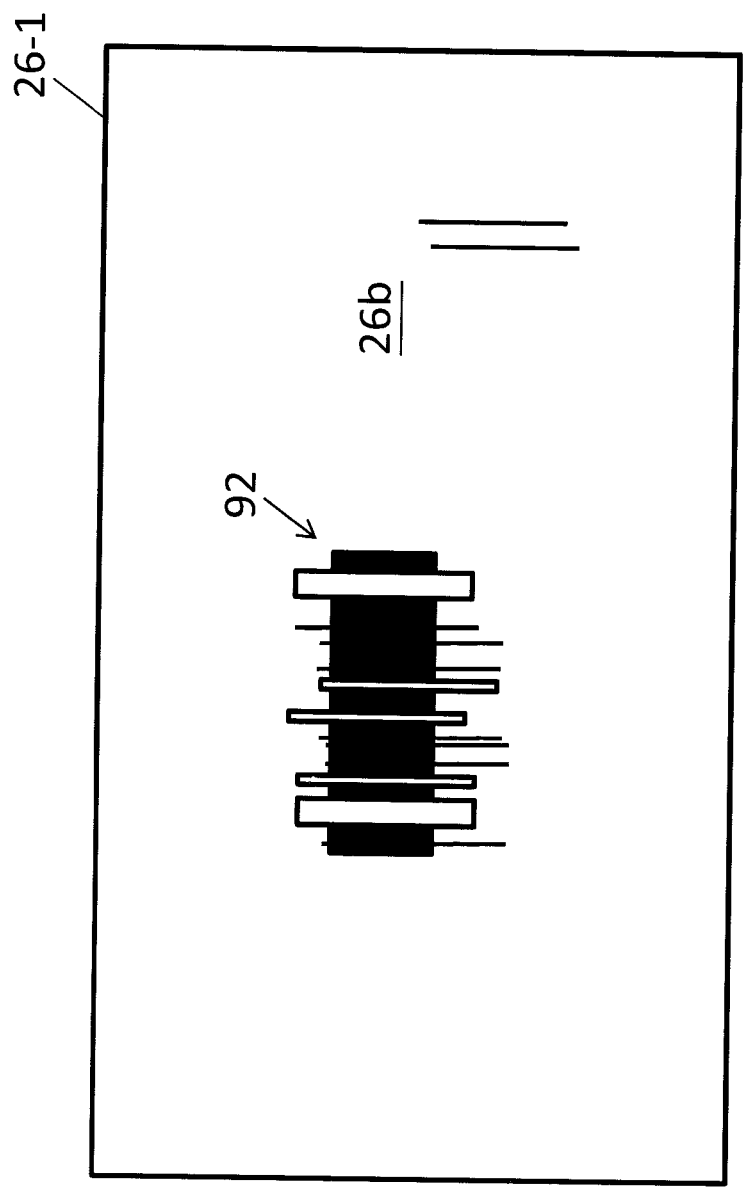
FIG. 9A is a bottom view of the first object illustrated in FIG. 8A.

FIG. 9A is a bottom view of the first object 26-1 illustrated in FIG. 8A. Referring to FIG. 9A, a bar code 92 may be printed on a bottom surface 26b of the object 26-1 along the first direction. The bar code 92 may distinguish the object 26-1 from other objects. To identify a bar code of a panel, as previously discussed, a second sensor may be provided at a suitable position in the platform 21.

Figure 9B:
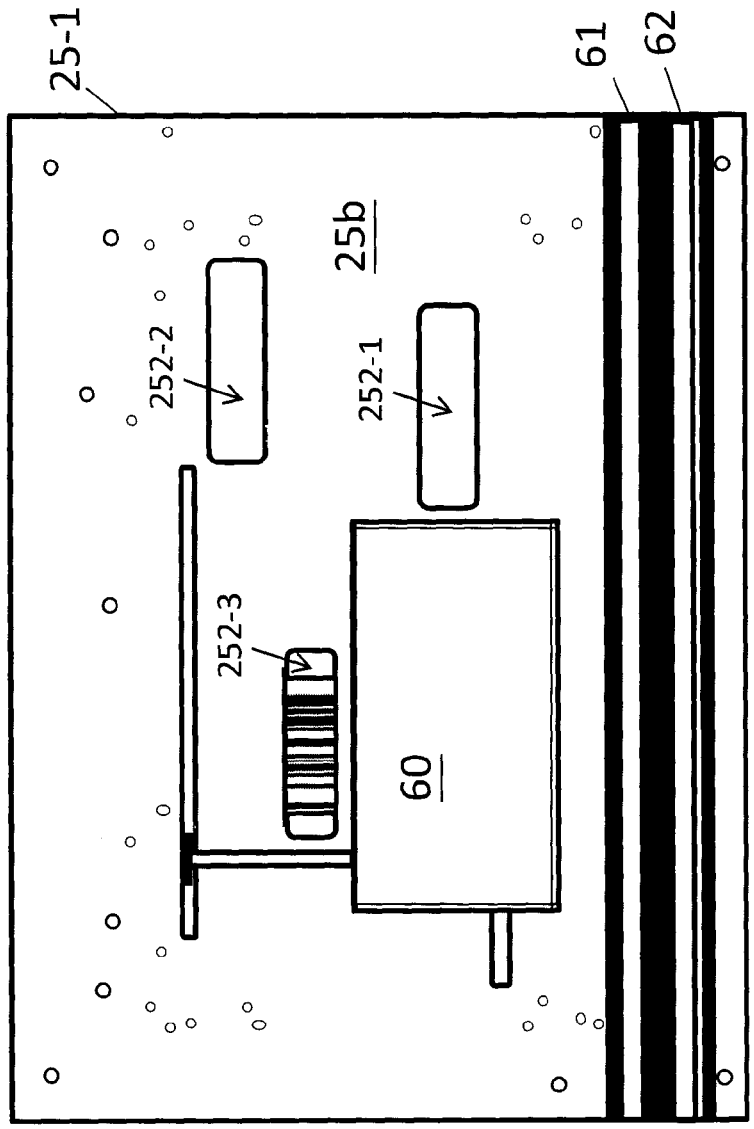
FIG. 9B is a bottom view showing the carrier when the first object is secured thereto.

FIG. 9B is a bottom view showing the carrier 25-1 when the first object 26-1 is secured thereto. Referring to FIG. 9B, one of the second openings 252 of a predetermined pattern may expose the bar code 92 of the first object 26-1. The bar code 92 may be detected by the second sensor and then sent to the controller 27.

It will be appreciated by those skilled in the art that changes could be made to the examples described above without departing from the broad inventive concept thereof It is understood, therefore, that this invention is not limited to the particular examples disclosed, but it is intended to cover modifications within the spirit and scope of the present invention as defined by the appended claims.

Further, in describing representative examples of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. An apparatus for optical inspection, the apparatus comprising:
   a platform extending in a first direction;
   a transmitting unit for transporting at least one carrier in the first direction from an input port to an output port thereof, each of the at least one carrier to support one of at least one object to be inspected;
   a first detector disposed above the platform and extending in a second direction orthogonal to the first direction for inspecting the at least one object on the at least one carrier, the first detector including a first scanner extending in the second direction between the input port and the output port, and a second scanner extending in the second direction between the first scanner and the output port, the first scanner including a plurality of scanning units arranged in the second direction that are sufficient to cover a width of the at least one object in the second direction;
   a first roller set between the first scanner and the input port to apply force onto a surface of each of the at least one object;
   a second roller set between the second scanner and the output port to apply force onto a surface of each of the at least one object; and
   at least one of a first angle adjusting means to adjust an angle of the first scanner with respect to the normal direction of the surface of each of the at least one object or a second angle adjusting means to adjust an angle of the second scanner with respect to the normal direction of each of the at least one object.

2. The apparatus of claim 1, wherein each of the at least one object includes a liquid crystal display (LCD) panel, and wherein each of the at least one carrier has a plurality of first openings on a first surface thereof to allow each of the at least one carrier to support panels of different sizes.

3. The apparatus of claim 2, wherein each of the at least one carrier has a plurality of second openings on the first surface to expose a bar code of the panel.

4. The apparatus of claim 2, wherein each of the at least one carrier includes a power control unit on a second surface thereof to control supply of power to the panel.

5. The apparatus of claim 4, wherein each of the at least one carrier includes a pair of conducting rails on the second surface to electrically couple the power control unit to a power source via the transmitting unit as each of the at least one carrier is transported by the transmitting unit.

6. The apparatus of claim 1, wherein at least one of the first roller set or the second roller set is allowed to move in a third direction orthogonal to a plane formed by the first direction and the second direction.

7. The apparatus of claim 1, wherein at least one of the first roller set or the second roller set includes a single roller having one of straight grooves and diagonal grooves on a roller surface.

8. The apparatus of claim 1, wherein at least one of the first roller set or the second roller set includes a plurality of rollers each being allowed to move in a third direction orthogonal to a plane formed by the first direction and the second direction.

9. The apparatus of claim 1 further comprising a cleaner disposed above the platform between the input port of the transmitting unit and the first scanner of the first detector and extending in the second direction.

10. The apparatus of claim 1 further comprising a second detector disposed above the platform between the input port and the first detector and extending in the second direction.

* * * * *